US012611307B2

(12) United States Patent
Pitkin et al.

(10) Patent No.: US 12,611,307 B2
(45) Date of Patent: Apr. 28, 2026

(54) LOAD-BEARING SKIN AND BONE INTEGRATED PYLON WITH HERMETICALLY SEALED NEURAL INTERFACE

(71) Applicants: Mark Pitkin, Sharon, MA (US); Grigory Raykhtsaum, Sharon, MA (US)

(72) Inventors: Mark Pitkin, Sharon, MA (US); Grigory Raykhtsaum, Sharon, MA (US)

(73) Assignee: Poly-Orth International, Sharon, MA (US)

( * ) Notice: Subject to any disclaimer, the term of this patent is extended or adjusted under 35 U.S.C. 154(b) by 0 days.

(21) Appl. No.: 19/266,836

(22) Filed: Jul. 11, 2025

(65) Prior Publication Data

US 2025/0339276 A1 Nov. 6, 2025

Related U.S. Application Data

(63) Continuation of application No. 29/846,117, filed on Jul. 13, 2022, now abandoned.

(51) Int. Cl.
*A61F 2/72* (2006.01)
*A61F 2/30* (2006.01)
*A61F 2/78* (2006.01)

(52) U.S. Cl.
CPC ............ *A61F 2/30749* (2013.01); *A61F 2/72* (2013.01); *A61F 2/78* (2013.01);
(Continued)

(58) Field of Classification Search
CPC .......... A61F 2/30756; A61F 2/70; A61F 2/72; A61F 2/78; A61F 2/2814; A61F 2/30749;
(Continued)

(56) References Cited

U.S. PATENT DOCUMENTS 5,376,139 A 12/1994 Pitkin
5,866,851 A 2/1999 Taylor et al.
(Continued)

OTHER PUBLICATIONS

Mark Pitkin et al., Transforming the Anthropomorphic Passive Free-Flow Foot Prosthesis Into a Powered Foot Prosthesis With Intuitive Control and Sensation (Bionic FFF), Military Medicine, Oct. 2024, pp. 439-447, vol. 189-3, Oxford University Press, US.
(Continued)

*Primary Examiner* — Sarah W Aleman
(74) *Attorney, Agent, or Firm* — Hinckley Allen & Snyder; Stephen Holmes

(57) ABSTRACT

The present invention incorporates a neural interface with a skin and bone integrated device with hermetic seal to prevent infection migration through the interface. The neural interface consists of plurality of wires that conduct signals between the inside body nerve system and the outside robotic/prosthetic mechanisms and controls. Each wire is electrically insulated through the channel of a single, double or multi bore insulator rod. The wires are extended outside on both ends of the rod forming leads for further connection with corresponding wires conducting signals to and from outside and inside body. The rod assembly is inserted inside a channel of a solid tubular load bearing titanium frame. The outside of the ceramic rod is hermetically brazed to the inside of the frame at both ends. The solid tubular frame is surrounded by a porous titanium portion of the pylon ensuring the integration with the skin.

12 Claims, 2 Drawing Sheets

(52) U.S. Cl.
    CPC .............. *A61F 2002/30589* (2013.01); *A61F*
                  *2002/30733* (2013.01); *A61F 2002/7887*
                                          (2013.01)

(58) Field of Classification Search
    CPC ................... A61F 2/60; A61F 2/30767; A61F
                  2220/0008; A61F 2220/0025; A61F
                  2002/30589; A61F 2002/30622; A61F
                  2002/30667; A61F 2002/30668; A61F
                                          2002/7887
    See application file for complete search history.

(56)                References Cited

U.S. PATENT DOCUMENTS

| | | | |
|---|---|---|---|
| 6,290,730 | B1 | 9/2001 | Pitkin et al. |
| 8,075,630 | B2 * | 12/2011 | Ricci ................. A61M 39/0247 |
| | | | 623/23.49 |
| 8,257,435 | B2 | 9/2012 | Pitkin et al. |
| 8,386,047 | B2 | 2/2013 | Koester |
| 8,992,615 | B2 | 3/2015 | Pitkin |
| 9,033,863 | B2 | 5/2015 | Jarvik |
| 9,308,103 | B1 * | 4/2016 | Kluger ...................... A61F 2/60 |
| 9,576,222 | B2 | 2/2017 | Nagayoshi |
| 9,579,222 | B2 | 2/2017 | Nagayoshi |
| 9,937,064 | B2 | 4/2018 | Poore et al. |
| 10,471,266 | B2 | 11/2019 | Morioka et al. |
| 11,173,053 | B2 | 11/2021 | Colvin et al. |
| 11,406,816 | B2 * | 8/2022 | Madeira .................... A61B 5/24 |
| 2004/0103906 | A1 * | 6/2004 | Schulman ................ A61B 5/07 |
| | | | 128/899 |
| 2013/0166009 | A1 * | 6/2013 | Branemark ........... A61F 2/2814 |
| | | | 607/149 |
| 2015/0305897 | A1 * | 10/2015 | Hershberger ......... A61F 2/2814 |
| | | | 623/32 |
| 2016/0030753 | A1 | 2/2016 | Shah et al. |
| 2019/0254845 | A1 * | 8/2019 | Wernke .................... A61F 2/72 |

OTHER PUBLICATIONS

Mark Pitkin et al., Transforming the Anthropomorphic Passive Free-Flow Foot Prosthesis Into a Powered Foot Prosthesis With Intuitive Control and Sensation (Bionic FFF), MHSRS-23-09579, Jul. 2025.

Willowwood META Flow, Product Highlights, 2024, https://www.willowwood.com/education-resources/resources/patents/.

Hangue Park et al., Electrical Stimulation of Distal Tibial Nerve During Stance Phase of Walking May Reverse Effects of Unilateral Paw Pad Anesthesia in the Cat, Motor Control, Oct. 2023, pp. 71-95, vol. 27-1, Human Kinetics, Inc.

Samuel K. Au and Hugh M. Herr, Powered ankle-foot prosthesis, IEEE Robotics & Automation Magazine, Sep. 2008, pp. 52-59, vol. 15-3, IEEE.

Miniature Linear Motion Series, Actuonix Motion Devices, 2019, Canada.

Mark Pitkin et al., Recent Progress in Animal Studies of the Skin- and Bone-integrated Pylon With Deep Porosity for Bone-Anchored Limb Prosthetics With and Without Neural Interface, Military Medicine, Feb. 2021, pp. 688-695, vol. 186-1, AMSUS.

Hangue Park et al., A real-time closed-loop control system for modulating gait characteristics via electrical stimulation of peripheral nerves, 2016, pp. 95-99, IEEE Xplore.

Hangue Park et al., A Prototype of a Neural, Powered, Transtibial Prosthesis for the Cat: Benchtop Characterization, Frontier in Nueroscience, Jul. 2018, pp. 1-13, vol. 12, Texas, US.

Max Ortiz-Catalan et al., Self-Contained Neuromusculoskeletal Arm Prostheses, Apr. 2020, pp. 1732-1738, vol. 18, Massachusetts, US.

Gillatt S. Kunutsor et al., Systematic review of the safety and efficacy of osseointegration prosthesis after limb amputation. British Journal of Surgery, pp. 1731-1741, vol. 105(13).

* cited by examiner

US 12,611,307 B2

1

LOAD-BEARING SKIN AND BONE INTEGRATED PYLON WITH HERMETICALLY SEALED NEURAL INTERFACE

CROSS-REFERENCE TO RELATED APPLICATIONS

This application is a continuation of U.S. patent application Ser. No. 29/846,117, filed Jul. 13, 2022.

BACKGROUND OF THE DISCLOSURE

(1) Field of the Invention

The instant invention relates to a load bearing skin and bone integrated prosthetic implantable device.

(2) Description of Related Art

Electro-mechanical and electronic systems are a common part of modern implantable devices. Numerous patents, for example, U.S. Pat. Nos. 5,866,851, 8,386,047, 9,033,863, 10,471,266, as well as patent application US2016/0030753, all teach hermetically sealed electrical components of the implants. These devices are fully implanted in the human body; they include such implants as pulse generators, pacemakers, blood pumps, cochlear devices, etc., and bear no load. The hermetic seals prevent the contact of electronic components with body tissue and fluids and are achieved in many cases by braze joints.

An additional challenge in achieving a protective seal between the body and the environment is associated with technology of direct skeletal attachment of limb prostheses. That technology, also called osseointegration (OI), uses an intermediate component called abutment partially implanted into the remnant of the residuum's bone, whereas its other part penetrates the residuum's skin as a means for attachment of the arm or leg prosthesis.

While the OI technology proven to be a valuable alternative to traditional residuum-socket-prosthesis attachment, the skin-abutment interface is a potential source of infection jeopardizing the long-term rehabilitation outcomes. A systematic review of 22 articles comprising 13 unique studies in OI showed a wide range of the infection rate, from 1 to 77 percent, and concluded that the current technology is associated with an increased risk of soft tissue infection. Even more difficult is to provide sufficient protective seal against outside infection, when the abutment has longitudinal channels for electrical wires/cables transmitting signals from nerves/muscles to the control system of the powered prosthesis.

U.S. Pat. No. 9,937,064 describes osseointegrated neural interface, however, does not teach the hermetic seal features. There is always a real possibility of infection penetrating through neural interface from outside environment into the body if the interface is not adequately sealed.

The recent U.S. Pat. No. 9,579,222 describes the prosthetic bone implant that contains a sealed neural interface. According to the patent the seal is achieved by screw joints. This patent appears to be successfully realized in arm prostheses as reported by Max Ortiz-Catalan, at al. in The New England Journal of Medicine, Apr. 30, 2020, pp. 1732-1738. A screw joint is not a hermetic seal as there is a physical gap between opposite threads. This gap may even increase with time. The presence of such a gap provides a possible path for infection migration from outside environment into the body.

SUMMARY OF THE DISCLOSURE

The present invention proposes a load bearing skin and bone integrated prosthetic implantable device as initially described in U.S. Pat. No. 8,257,435. A portion of such a device is implanted into a human body, more specifically, into a bone of a limb, whereas the remaining portion stays outside the body, and is exposed to the environment.

In addition, the present disclosure refers to a neural interface as a mean of conducting/transmitting electrical signals between the body and the outside robotic/prosthetic motion mechanisms and controls.

Moreover, the present disclosure refers to a hermetically sealed neural interface.

According to exemplary embodiments of the invention, the skin integration as described in U.S. Pat. No. 8,257,435 provides an infection barrier between the outside environment and osseointegrated implant inside the body. The object of present invention is to incorporate the neural interface with such a device and provide the neural interface hermetic seal to prevent the infection migration through the interface.

The neural interface may consist of plurality of electrically conductive wires that conduct the signals between the inside body nerve system and the outside robotic motion mechanisms and controls. The neural interface wires may be made with medically approved alloys such as stainless steel, MP35, pure and alloyed platinum.

Each of such wires is electrically insulated. This is achieved by threading each wire through the channel of a single, double or multi bore insulator rod, for example a ceramic rod, that may be made with alumina (similar to a multi-bore rod that is used for thermocouple housing). All said wires are extended outside on both ends of the rod forming leads for further connection with corresponding wires conducting signals to and from outside and inside body. The wires are hermetically braze-sealed to inside of each bore at both ends of the ceramic rod.

The assembly of wires and ceramic rod is inserted inside channel of the solid tubular load bearing frame that is made with pure or alloyed titanium. The tubular frame length defines the direction of implantation. The outside of the ceramic rod is hermetically brazed to the inside of the frame at the ends. The solid tubular frame is surrounded by a porous titanium portion of the pylon ensuring the integration with skin.

The tubular frame is load bearing, and therefore may deform (flexed/bowed) under excessive loads to the extend where the ceramic rod insert inside may crack. To improve the flexibility of the ceramic insert it may be replaced by a stock of single, double or multi bore ceramic discs or cylinders, so that only one disc or cylinder on each end are hermetically brazed.

For brazing both the ceramic to titanium and ceramic to conducting wires the preforms and pastes of biocompatible gold-titanium filler metal may be used.

The assembling sequence of the whole pylon device is as follows:

1. The pylon consisting of solid pure or alloyed titanium tubular frame and compacted titanium powders surrounding the frame is sintered according to U.S. Pat. No. 8,257,435.

2. A ceramic insert with threaded wires is placed inside the channel of the tubular frame.

3. A short time brazing cycle that requires the temperature lower than the temperature of titanium sintering is applied. This cycle conditions do not affect the structure of the pylon.

Thus, such an assembly provides skin and bone integration in combination with hermetically sealed neural interface such that the propagation of the infection from outside is blocked.

The wires that extend from both ends of the pylon are not insulated and may be sealed from each other by means of PEEK thermoplastic or long-term implantable silicone as described in U.S. Pat. No. 9,579,222.

Depending on the size of the pylon and the diameter size of the interface wires, the connection to the wires coming from inside and outside the body can be done in different ways. For example, if the interface wires are thin, then the connection can be achieved by crimping. The crimped connection can be also sealed with PEEK or silicone. In the second example, where the interface wires are thick and stiff, a special connector device may be used with the option of securing connection by screwing the connector assembly to a pylon frame.

In the situations when the use of biocompatible epoxy, PEEK or silicone is permissible to be used for sealing the neural interface, the high temperature brazing operation may be avoided. The interface wires are then coated, for example with PTFE, to provide electrical insulation. The separate wires or their braid may be placed inside the channel of the tubular frame and then sealed at the frame ends at room temperature.

While embodiments of the invention have been described as having the features recited, it is understood that various combinations of such features are also encompassed by particular embodiments of the invention and that the scope of the invention is limited by the claims and not the description.

BRIEF DESCRIPTION OF THE DRAWINGS

While the specification concludes with claims particularly pointing out and distinctly claiming particular embodiments of the instant invention, various embodiments of the invention can be more readily understood and appreciated from the following descriptions of various embodiments of the invention when read in conjunction with the accompanying drawings in which:

DETAILED DESCRIPTION OF THE EXEMPLARY EMBODIMENTS

Certain exemplary embodiments will now be described to provide an overall understanding of the principles of the structure, function, manufacture, and use of the device and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present disclosure. Further, in the present disclosure, like-numbered components of the embodiments generally have similar features, and thus within a particular embodiment each feature of each like-numbered component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Further, to the extent that directional terms like top, bottom, up, or down are used, they are not intended to limit the systems, devices, and methods disclosed herein. A person skilled in the art will recognize that these terms are merely relative to the system and device being discussed and are not universal.

Figures 1, 2, 3:
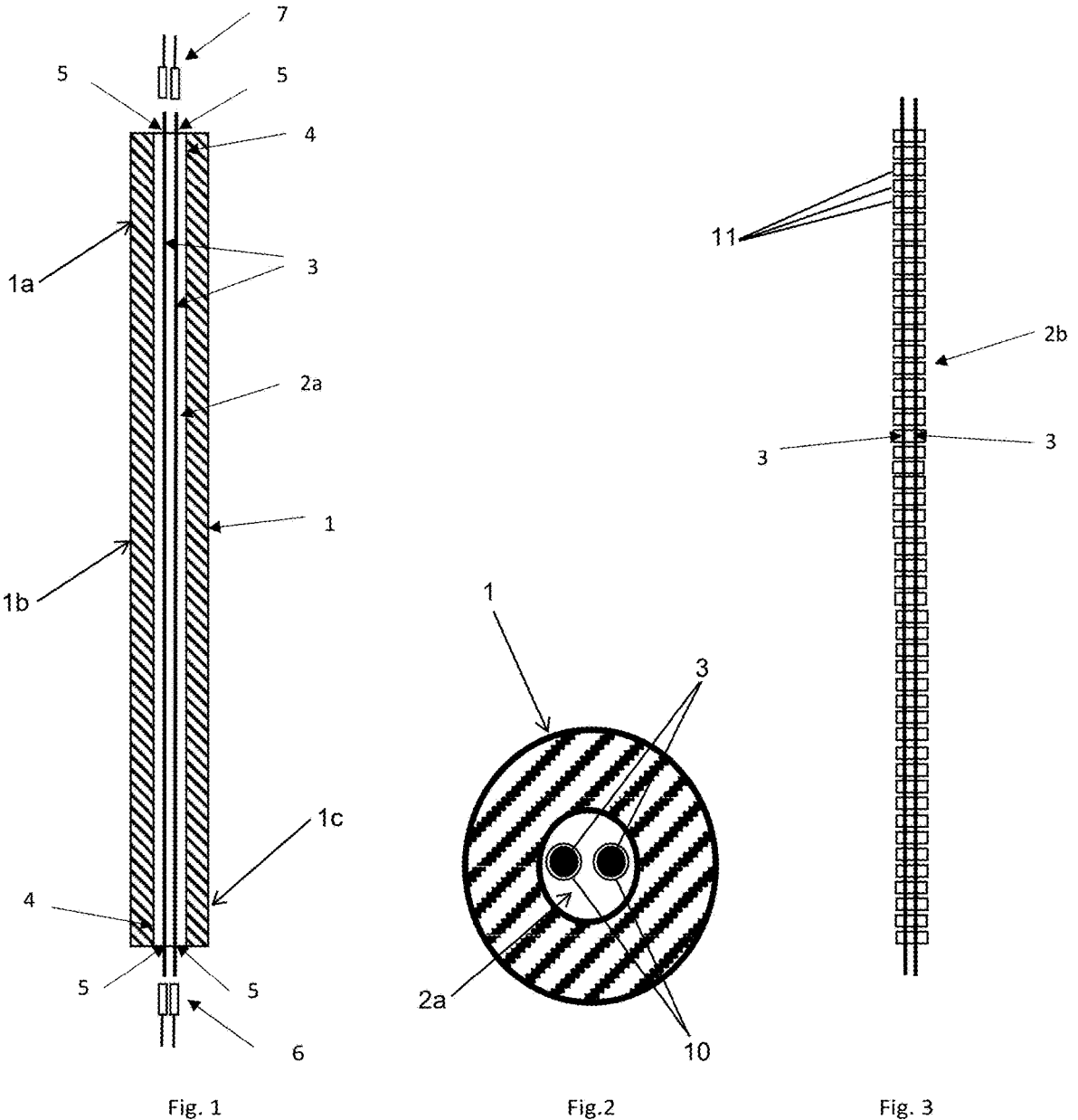
FIG. 1 shows a longitudinal cross section of the pylon solid frame.
FIG. 2 is transversal cross section of the pylon solid frame.
FIG. 3 shows a disc or cylinder assembly of ceramic insert.

The overview of the hermetically sealed neural interface is illustrated in FIG. 1. The ceramic single, double or multi bore insert 2a or 2b (shown in FIG. 3) is placed inside the tubular solid pylon frame 1. The pylon frame 1 has an inner portion 1a frame adapted to be positioned inside a bone of a limb's residuum, an outer portion 1c adapted to be positioned outside the limb's residuum, and a middle portion 1b between the inner portion and the outer portion adapted to be positioned at a skin layer of the limb's residuum. The middle portion 1c further includes a porous permeable body 8 comprising compacted and sintered particles filling in regions around the solid tubular frame wherein, in the middle portion 1c, the porosity of the volume fraction of the compacted and sintered particles is within a range of about 30% to about 50%, wherein the compacted and sintered particles have a particle size within the range of about 20 to about 500 microns and a pore size between the compacted and sintered particles is in a range of about 20 to about 350 microns. The length of the ceramic insert 2a or 2b equals the length of the pylon frame 1. The conducting wires 3 are threaded through the bores 10 of the ceramic insert 2a or 2b (See FIG. 2).

The neural interface may consist of plurality of electrically conductive wires 3 that conduct the signals between the inside body nerve system and the outside robotic motion mechanisms and controls. The neural interface wires 3 may be made with medically approved alloys such as stainless steel, MP35, pure and alloyed platinum. Each of such wires is electrically insulated. This is achieved by threading each wire through the channel of a single, double or multi bore insulator rod, for example a ceramic rod, that may be made with alumina (similar to a multi-bore rod that is used for thermocouple housing). All said wires are extended outside on both ends of the rod forming leads for further connection with corresponding wires conducting signals to and from outside and inside body. The wires are hermetically braze-sealed to inside of each bore at both ends of the ceramic rod.

Areas 4 are the braze joints between ceramic insert 2a or 2b and pylon frame 1 at both ends of pylon frame 1. Areas 5 are the braze joints between the ceramic insert 2a or 2b and the wires 3 at both ends of pylon frame 1. For brazing both the ceramic to titanium and ceramic to conducting wires the preforms and pastes of biocompatible gold-titanium filler metal may be used. Connecting wires 6 (from outside robotic motion mechanisms and controls) and wires 7 (from inside body nerve system) are not the part of the present invention and are shown for reference only. The circular shape of the pylon solid frame 1 and of the ceramic insert 2a or 2b are illustrated by a transversal cross section of the pylon solid frame 1 in FIG. 2. The tubular pylon frame 1 may also have an oval shape.

FIG. 3 illustrates the more flexible option 2b as a stack of ceramic discs or cylinders 11 with threaded through wires 3. The tubular frame 1 is load bearing and therefore may deform (flexed/bowed) under excessive loads to the extend where the ceramic rod 2a insert inside may crack. To improve the flexibility of the ceramic insert it may be replaced by a stock of single, double or multi bore ceramic discs or cylinders 11, so that only one disc or cylinder on each end are hermetically brazed.

Figures 4, 5, 6:
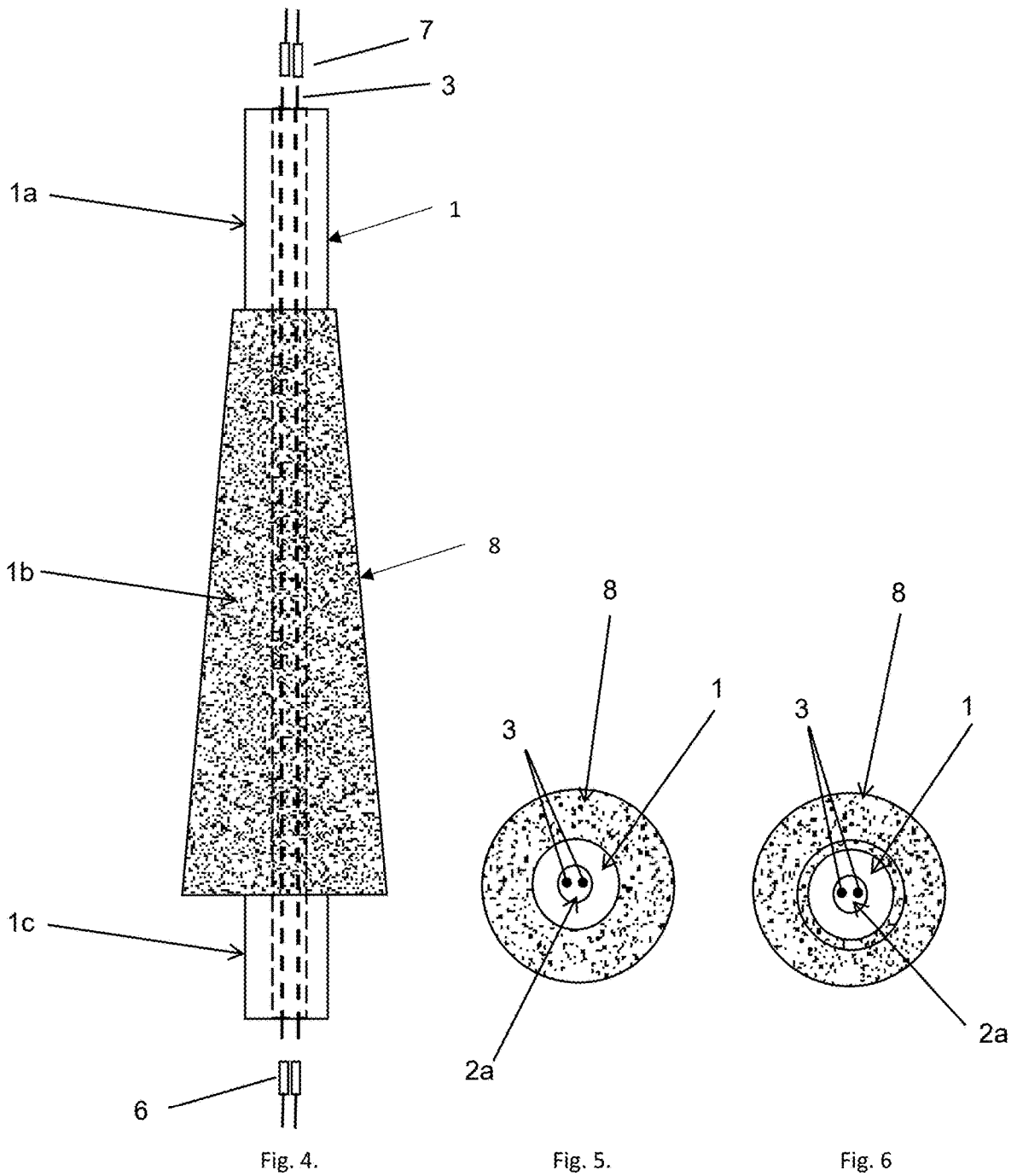
FIG. 4 shows a side view of the load bearing skin and bone integrated pylon with hermetically sealed neural interface.
FIG. 5 is a bottom view of a pylon shown in FIG. 4.
FIG. 6 is a top view of a pylon shown in FIG. 4.

The side view of the complete pylon is shown in FIG. 4. It illustrates the configuration of solid frame 1 and porous portion 8. Corresponding bottom and top views of the pylon shown in FIG. 4 are shown in FIGS. 5 and 6 respectively.

While there is shown and described herein certain specific structures embodying various embodiments of the invention, it will be manifest to those skilled in the art that various modifications and rearrangements of the parts may be made without departing from the spirit and scope of the underlying inventive concept and that the same is not limited to the particular forms herein shown and described except insofar as indicated by the scope of the appended claims.

What is claimed is:

1. A load bearing skin and bone integrated pylon comprises:

a load-bearing solid tubular frame elongated in the direction of implantation, and adapted to carry body weight, forces, and moments associated with locomotion, wherein an inner portion of the solid tubular frame is adapted to be positioned inside a bone of a limb's residuum and an outer portion of the solid tubular frame is adapted to be positioned outside the limb's residuum to receive a prosthesis, and a middle portion of the solid tubular frame between the inner portion and the outer portion is adopted to be positioned at a skin layer of the limb's residuum, the middle portion further comprising a porous permeable body comprising compacted and sintered particles filling in regions around the solid tubular frame wherein, in the middle portion, the porosity of the volume fraction of the compacted and sintered particles is within a range of about 30% to about 50%, wherein the compacted and sintered particles have a particle size within the range of about 20 to about 500 microns and a pore size between the compacted and sintered particles is in a range of about 20 to about 350 microns;

an insulator insert positioned inside the solid tubular frame, and having approximately the same length as said solid tubular frame, said insulator insert having at least one bore extending therethrough, wherein a hermetic seal is formed between the insert and the solid tubular frame on both ends; and a plurality of electrically conductive wires each threaded through the entire length of said at least one bore of the insert;

wherein each of the ends of the electrically conductive wires extend outside the insert, forming leads for further connection;

wherein a hermetic seal is formed between each end of the conductive wires and the at least one bore of the insert.

2. The load-bearing skin and bone integrated pylon of claim 1, wherein a load-bearing solid tubular frame is made with biocompatible material.

3. The load-bearing skin and bone integrated pylon of claim 1, wherein a load-bearing solid tubular frame is made with pure or alloyed titanium.

4. The load-bearing skin and bone integrated pylon of claim 1, wherein a load-bearing solid tubular frame has a circular transversal shape.

5. The load-bearing skin and bone integrated pylon of claim 1, wherein a load-bearing solid tubular frame has an oval transversal shape.

6. The load-bearing skin and bone integrated pylon of claim 1, wherein compacted and sintered particles are made with biocompatible material.

7. The load-bearing skin and bone integrated pylon of claim 1, wherein compacted and sintered particles are made with pure or alloyed titanium.

8. The load-bearing skin and bone integrated pylon of claim 1, wherein said insulator insert is made with the biocompatible ceramic material.

9. The load-bearing skin and bone integrated pylon of claim 1, wherein said insulator insert is made with the alumina.

10. The load-bearing skin and bone integrated pylon of claim 1, wherein a hermetic seal is formed by brazing.

11. The load-bearing skin and bone integrated pylon of claim 1, wherein a hermetic seal is formed by epoxy.

12. The load-bearing skin and bone integrated pylon of claim 1, wherein said insulator insert comprises a stack of ceramic discs or cylinders.

* * * * *